(12) United States Patent
Messana et al.

(10) Patent No.: US 9,828,327 B2
(45) Date of Patent: Nov. 28, 2017

(54) ANAEROBIC CURABLE COMPOSITIONS CONTAINING BLOCKED DICARBOXYLIC ACID COMPOUNDS

(71) Applicant: Henkel IP & Holding GmbH, Duesseldorf (DE)

(72) Inventors: Andrew D. Messana, Newington, CT (US); Sean M. Burdzy, Hamden, CT (US); Joel D. Schall, Hamden, CT (US); Anthony F. Jacobine, North Haverhill, NH (US)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 15/340,435

(22) Filed: Nov. 1, 2016

(65) Prior Publication Data
US 2017/0044089 A1    Feb. 16, 2017

Related U.S. Application Data

(63) Continuation of application No. PCT/US2015/028822, filed on May 1, 2015.
(Continued)

(51) Int. Cl.
*C08F 20/06* (2006.01)
*C08F 118/02* (2006.01)
(Continued)

(52) U.S. Cl.
CPC .............. *C07C 69/60* (2013.01); *C07C 69/54* (2013.01); *C08F 2/44* (2013.01); *C08F 220/28* (2013.01);
(Continued)

(58) Field of Classification Search
CPC .... C08F 2/44; C08F 220/28; C08F 2220/281; C08F 2220/286; C08F 222/06;
(Continued)

(56) References Cited

U.S. PATENT DOCUMENTS

| 3,970,505 A | 7/1976 | Hauser et al. |
| 4,215,209 A | 7/1980 | Meier et al. |

(Continued)

FOREIGN PATENT DOCUMENTS

| WO | 9901484 | 1/1999 |
| WO | 2009014688 | 1/2009 |

(Continued)

OTHER PUBLICATIONS

International Search Report issued in connection with International Patent Application No. PCT/US2015/028908 dated Aug. 27, 2015.
(Continued)

*Primary Examiner* — William Cheung
(74) *Attorney, Agent, or Firm* — Steven C. Bauman

(57) ABSTRACT

Anaerobic curable compositions, such as adhesives and sealants, containing blocked dicarboxylic acid compounds are provided. The blocked dicarboxylic acid compounds are labile dicarboxylic acid compounds having two acetal linkages, which cleave to release the underlying dicarboxylic acid during anaerobic cure. In this way, the dicarboxylic acid can participate in the anaerobic cure of the composition when the blocking group is released.

6 Claims, 1 Drawing Sheet

Related U.S. Application Data

(60) Provisional application No. 62/061,389, filed on Oct. 8, 2014, provisional application No. 61/987,201, filed on May 1, 2014.

(51) Int. Cl.
| | | |
|---|---|---|
| *C07C 69/60* | (2006.01) | |
| *C08F 2/44* | (2006.01) | |
| *C08F 220/28* | (2006.01) | |
| *C09J 133/06* | (2006.01) | |
| *C08L 33/06* | (2006.01) | |
| *C09J 133/14* | (2006.01) | |
| *C07C 69/54* | (2006.01) | |

(52) U.S. Cl.
CPC .............. *C08L 33/06* (2013.01); *C09J 133/06* (2013.01); *C09J 133/14* (2013.01); *C08F 2220/281* (2013.01); *C08F 2220/286* (2013.01)

(58) Field of Classification Search
CPC ....... C09J 133/06; C09J 133/14; C08L 33/06; C07C 69/60; C07C 69/54
USPC ............................................... 526/317.1, 319
See application file for complete search history.

(56) References Cited

U.S. PATENT DOCUMENTS

| | | | |
|---|---|---|---|
| 4,287,350 A | 9/1981 | Huellstrung et al. | |
| 4,321,349 A | 3/1982 | Rich | |
| 4,324,349 A | 4/1982 | Kaufman | |
| 4,525,232 A | 6/1985 | Rooney et al. | |
| 5,411,988 A | 5/1995 | Bockow et al. | |
| 5,605,999 A | 2/1997 | Chu | |
| 6,048,587 A | 4/2000 | Estrin | |
| 7,728,092 B1 | 6/2010 | Jacobine et al. | |
| 7,951,884 B1 | 5/2011 | Birkett et al. | |
| 2005/0101689 A1* | 5/2005 | Woods ................... | C08F 20/28 522/178 |
| 2009/0281335 A1 | 11/2009 | Messana et al. | |
| 2012/0168219 A1 | 7/2012 | Kitamura et al. | |
| 2013/0289205 A1* | 10/2013 | Sugasaki ................. | B41N 1/12 524/854 |
| 2014/0004353 A1 | 1/2014 | Birkett et al. | |

FOREIGN PATENT DOCUMENTS

| | | |
|---|---|---|
| WO | 2011047123 | 4/2011 |
| WO | 2014043720 | 3/2014 |

OTHER PUBLICATIONS

R.D. Rich, "Anaerobic Adhesives" in Handbook of Adhesive Technology, 29, 467-79, A. Pizzi and K.L. Mittal, eds., Marcel Dekker, Inc., New York (1994).

International Search Report issued in connection with International Patent Application No. PCT/US2015/028829 dated Jun. 22, 2015.

International Search Report issued in connection with international Patent Application No. PCT/US2015/028822 dated Jun. 29, 2015.

\* cited by examiner

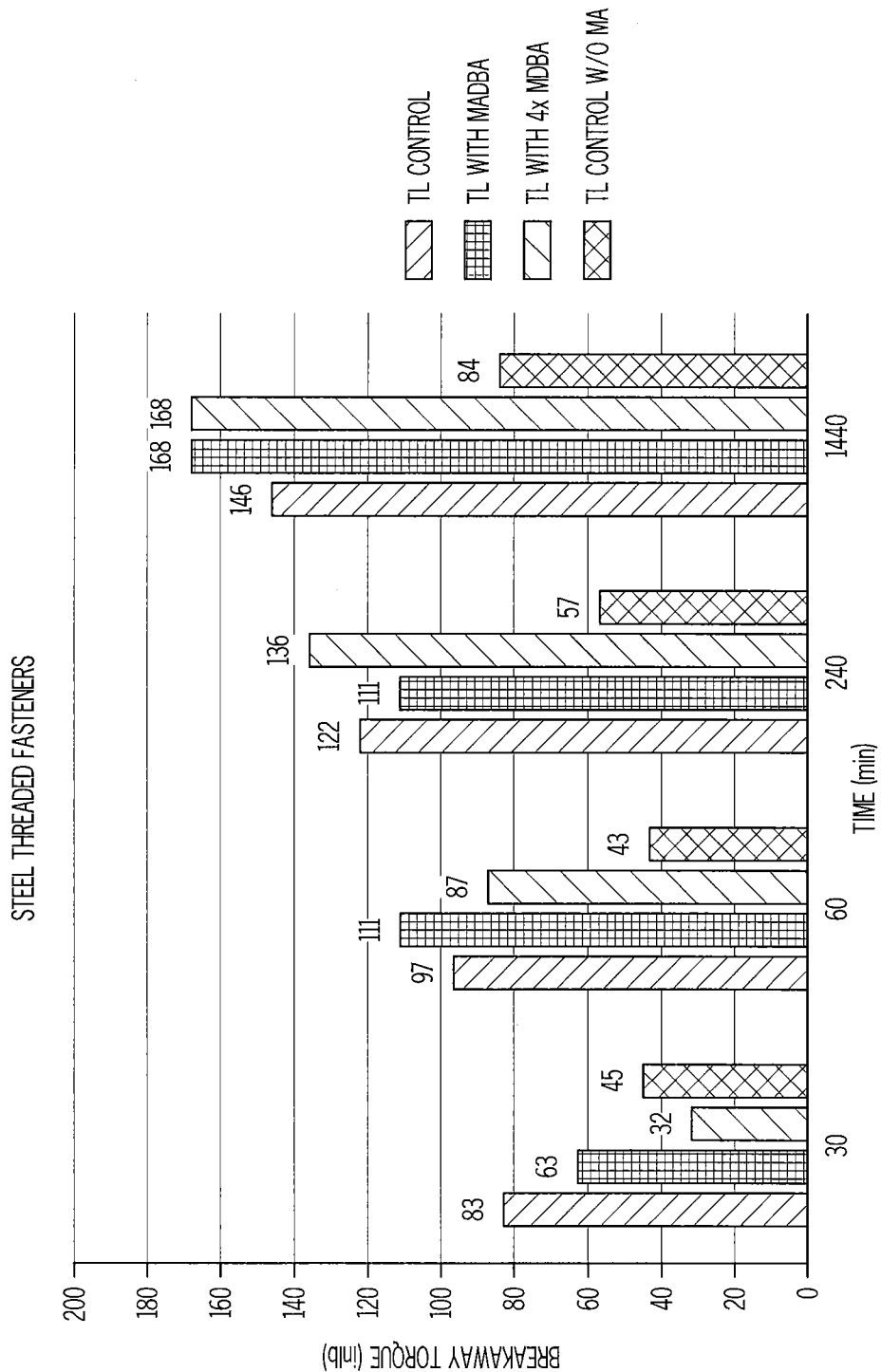

ANAEROBIC CURABLE COMPOSITIONS CONTAINING BLOCKED DICARBOXYLIC ACID COMPOUNDS

This application is a continuation of a US National Stage application under 35 USC 371 of PCT International Application No. PCT/US2015/028822, filed on May 1, 2015, which claims priority to, and the benefit of U.S. Provisional Patent Application No. 62/061,389, filed on Oct. 8, 2014, and U.S. Provisional Patent Application No. 61/987,201, filed on May 1, 2014, all of which are herein incorporated by reference in their entirety.

BACKGROUND

Field

Anaerobic curable compositions, such as adhesives and sealants, containing blocked dicarboxylic acid compounds are provided. The blocked dicarboxylic acid compounds are labile dicarboxylic acid compounds having two acetal linkages, which cleave to release the underlying dicarboxylic acid during anaerobic cure. In this way, the dicarboxylic acid can participate in the anaerobic cure of the composition when the blocking group is released.

Brief Description of Related Technology

Anaerobic adhesive compositions generally are well-known. See e.g., R. D. Rich, "Anaerobic Adhesives" in Handbook of Adhesive Technology, 29, 467-79, A. Pizzi and K. L. Mittal, eds., Marcel Dekker, Inc., New York (1994), and references cited therein. Their uses are legion and new applications continue to be developed.

Conventional anaerobic adhesive compositions ordinarily include a free-radically polymerizable acrylate ester monomer, together with a peroxy initiator and an inhibitor component. Oftentimes, such anaerobic adhesive compositions also contain accelerator components to increase the speed with which the composition cures. Additionally, such compositions may also include adhesion promoters, which can function to increase adhesion to substrates, thereby enhancing adhesive strength.

Maleic acid ("MA") is a commonly used accelerator, together with acetyl phenylhydrazine ("APH"), in anaerobic adhesive compositions. However, MA has limited solubility in some of these compositions, a prime example of which is LOCTITE 243, commercially available from Henkel Corporation, Rocky Hill, Conn.

In addition to its solubility limits, MA has the disadvantage of being heavily regulated due to its health and safety profile, and thus, requires special considerations during handling, storage, and disposal.

As a result of its limited solubility and regulatory scrutiny in certain parts of the world, efforts have been undertaken to identify replacements for MA. To date, these efforts have not provided an acceptable alternative.

It would thus be advantageous to enjoy the properties conferred upon anaerobic curable compositions by MA without the attendant environmental and safety concerns and sparing solubility properties. The present invention provides such a solution.

SUMMARY

In a broad sense, the present invention relates to anaerobic curable compositions, such as adhesives and sealants, containing blocked dicarboxylic acid compounds. The blocked dicarboxylic acid compounds are labile dicarboxylic acid compounds having two acetal linkages, which cleave to release the underlying dicarboxylic acid during anaerobic cure. In this way, the underlying dicarboxylic acid can participate in the anaerobic cure of the composition.

A labile dicarboxylic acid compound ("LDA") is a reaction product that has been prepared from a dicarboxylic acid and a compound containing at least one vinyl ether group. The so-formed reaction product provides an acetal compound having a structure represented by:

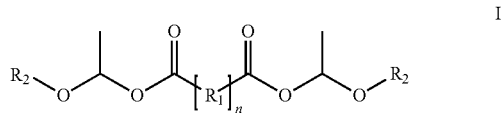

I where $R_1$ is an $C_{1-12}$ alkylene, $C_{2-12}$ alkenylene unit, or $C_{6-14}$ aryl; n is 0, 1 or 2; and $R_2$ are each individually selected from $C_{2-20}$ alkyl or alkenyl, $C_{5-14}$ cycloalkyl or cycloalkenyl, or $C_{6-14}$ aryl, each of which may be substituted or interrupted by one or more amine, hydroxyl, ether or vinyl ether groups or units.

In structure I the two acetal bonds are cleavable, and once cleaved release the underlying carboxylic acid to which a vinyl ether containing compound had been reacted to form the acetal blocking unit.

Generally, as noted above, MA is useful as an accelerator in anaerobic curable compositions. The LDA compounds are likewise useful as accelerators for anaerobic curable compositions, such as adhesives and sealants. The LDA compounds can assist to accelerate cure when exposed to anaerobic conditions appropriate to cure the composition. The blocking group is removed under the reaction conditions of anaerobic cure, thereby releasing the underlying dicarboxylic maleic acid to perform its cure accelerating function. In other words, anaerobic cure conditions cause the cleavage of the acetal bond and re-formation of in this case, MA, and the vinyl ether compound.

In one aspect, there is provided an anaerobic curable composition which includes:
  a (meth)acrylate component;
  an anaerobic cure system; and
  a compound within structure I.

In another aspect, there is provided an anaerobic curable composition comprising the reaction product of:
  a (meth)acrylate component;
  an anaerobic cure system; and
  a compound within structure I.

In another aspect, there is provided a method of anaerobically curing an anaerobic curable composition which includes:
  (i) providing a composition which includes:
    a (meth)acrylate component;
    an anaerobic cure system; and
    a compound within structure I;
  (ii) applying the composition of (i) to at least a portion of at least one surface of at least one substrate available for bonding;
  (iii) providing another substrate having a surface available for bonding in a mating relationship with the substrate of (ii); and
  (iv) exposing the at least one substrate of (ii) and the substrate of (iii) to anaerobic cure conditions appropriate to cure the composition and bond the substrates.

BRIEF DESCRIPTION OF THE FIGURES

The FIGURE shows a chart of breakaway torque measured against time for four compositions, two of which are controls (Compositions A and D) and two of which are within the scope of the present invention (Compositions B and C).

DETAILED DESCRIPTION

The term "labile dicarboxylic acid" or LDA is intended to include compounds which undergo a chemical change and revert to its starting materials, a dicarboxylic acid, such as maleic acid or itaconic acid, and a vinyl ether compound, during anaerobic cure. This term is used interchangeably with "blocked dicarboxylic acid".

As noted above, the LDA should have a structure represented by:

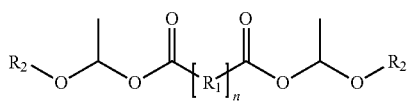

I where $R_1$ is an $C_{1-12}$ alkylene, $C_{2-12}$ alkenylene unit, or $C_{6-14}$ aryl; n is 0, 1 or 2; and $R_2$ are each individually selected from $C_{2-20}$ alkyl or alkenyl, $C_{5-14}$ cycloalkyl or cycloalkenyl, or $C_{6-14}$ aryl, each of which may be substituted or interrupted by one or more amine, hydroxyl, ether or vinyl ether groups or units.

Embraced by structure I therefore are where n=0, oxalic acid, and saturated dicarboxylic acids, such as where $R_1$ is a 1 carbon atom unit malonic acid, where $R_1$ is a 2 carbon atom unit succinic acid, where $R_1$ is a 3 carbon atom unit glutaric acid, where $R_1$ is a 4 carbon atom unit apidic acid, where $R_1$ is a 5 carbon atom unit pimelic acid, where $R_1$ is a 6 carbon atom unit suberic acid, where $R_1$ is a 7 carbon atom unit azelaic acid and where $R_1$ is a 8 carbon atom unit sebacic acid.

Specific examples of the underlying dicarboxylic acid where $R_1$ is an alkenylene unit may be selected from

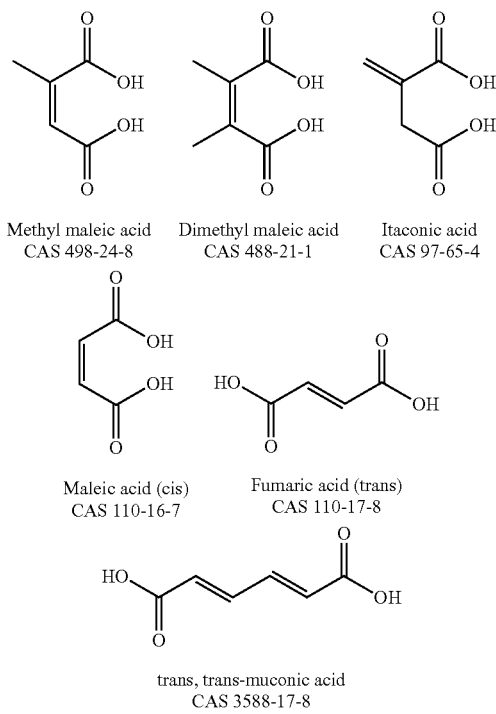

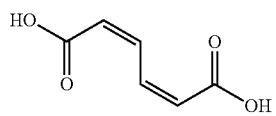

cis, cis-muconic acid
CAS 1119-72-8

The selection of a blocking unit to form the LDA compound is based on several considerations. One such consideration is the ability to "protect" or block the carboxylic acid group such that it prevents premature reaction with its surroundings, thereby alleviating health, safety and environmental concerns, all of which require special handling. Thus, the labile compound should be relatively stable under what would be generally considered normal storage, shelf life and manufacturing conditions for reactant ingredients.

This stability should however not prevent the cleavage of the blocking unit and reformation of underlying dicarboxylic acid during anaerobic cure. Thus, during preparation and storage of the LDA, the LDA remains substantially stable, and when incorporated into an anaerobic curable composition, this stability continues until the composition is subjected to anaerobic curing conditions. When subjected to anaerobic curing conditions the underlying dicarboxylic acid becomes unblocked and the underlying dicarboxylic acid is released to participate in the anaerobic cure. To achieve these properties, the underlying dicarboxylic acid is joined to the blocking unit—the chosen vinyl ether—via an acetyl linage.

Another consideration for selection of appropriate blocking units is the compatibility of the LDA with the anaerobic curable composition to which it will be added. Generally, the chosen LDA has good miscibility and/or solubility with (meth)acrylate monomers or resins that form the matrix of the anaerobic curable composition and does not react prematurely to any significant extent with any portion of the anaerobic curable composition. Moreover, once the blocking unit and the underlying dicarboxylic acid are separated, the blocking unit should not substantially deleteriously affect the anaerobic cure or substantially deleteriously affect the properties of the anaerobic curable composition or the final properties of the cured composition.

Desirably the underlying dicarboxylic acid is in liquid form or readily miscible and/or soluble with (meth)acrylate monomers or resins for ease of incorporation into the anaerobic curable composition. However, once the LDA is unblocked during anaerobic cure, the vinyl ether compound which acted as a blocking agent is available to participate in the anaerobic cure.

Desirable blocking units include vinyl ether compounds. Mono- and di-vinyl ether compounds are contemplated, non-limiting examples of which include those listed in Table I below. The vinyl ether ("VE") compounds may be used individually or in combination.

TABLE I

| VE No. | Compound | CAS No. | Structure |
|---|---|---|---|
| 1 | Ethyl vinyl ether | 109-92-2 | 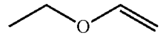 |
| 2 | Isobutyl vinyl ether | 109-53-5 | 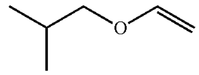 |
| 3 | N-Butyl vinyl ether | 111-34-2 | 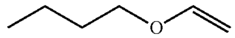 |
| 4 | tert-Butyl vinyl ether | 926-02-3 | 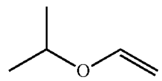 |
| 5 | Cyclohexyl vinyl ether | 2182-55-0 | 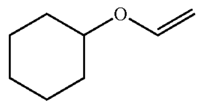 |
| 6 | 1,4-Cyclohexane dimethanol divinyl ether | 17351-75-6 | 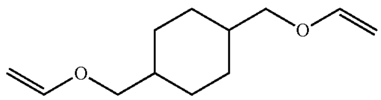 |
| 7 | Butanediol divinyl ether | 3891-33-6 | 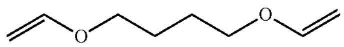 |
| 8 | Hydroxybutyl vinyl ether | 17832-28-9 | 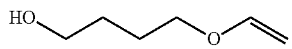 |
| 9 | Diethylene glycol divinyl ether | 764-99-8 | 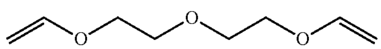 |
| 10 | Triethylene glycol divinyl ether | 765-12-8 | 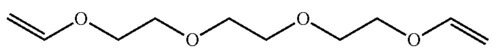 |
| 11 | Dodecyl vinyl ether | 765-14-0 | 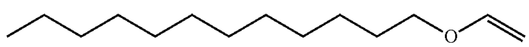 |
| 12 | Octadecyl vinyl ether | 930-02-9 | 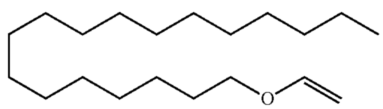 [SMILES: C=COCCCCCCCCCCCCCCCCCC] |
| 13 | 4-(Hydroxy methyl) cyclohexyl methyl vinyl ether | 114651-37-5 | 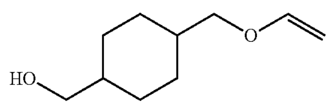 |
| 14 | 2-Ethyl hexyl vinyl ether | 103-44-6 | 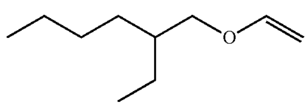 |
| 15 | Diethylene glycol monovinyl ether | 929-37-3 | 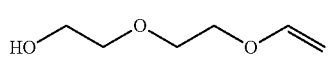 |
| 16 | Poly-THF 290-Divinyl ether | 486438-23-7 | 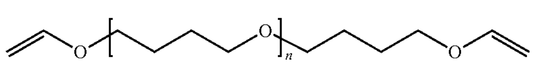 |
| 17 | 3-Amino propyl vinyl ether | 66415-55-2 | 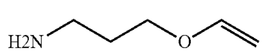 |
| 18 | Tert-Amyl vinyl ether | 29281-39-8 | 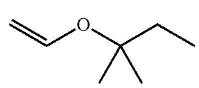 |
| 19 | Diethylaminoethyl vinyl ether | 3205-13-8 | 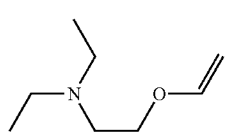 |

TABLE I-continued

| VE No. | Compound | CAS No. | Structure |
|---|---|---|---|
| 20 | Ethyleneglycol butyl vinyl ether | 4223-11-4 | 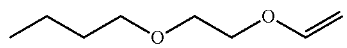 |
| 21 | Ethyleneglycol divinyl ether | 764-78-3 | 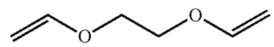 |
| 22 | Ethyleneglycol monovinyl ether | 764-48-7 | 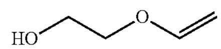 |
| 23 | Hexanediol divinyl ether | 19763-13-4 | 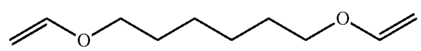 |
| 24 | Hexanediol monovinyl ether | 27336-16-9 | 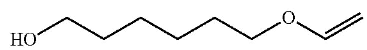 |
| 26 | Isopropyl vinyl ether | 926-65-8 | 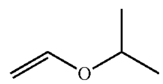 |
| 27 | Polyethyleneglycol-520 methyl vinyl ether | 50856-25-2 | $CH_2=CHO[CH_2CH_2O]_nCH_3$ |
| 28 | Pluriol-E200 divinyl ether | 50856-26-3 | $CH_2=CHO[CH_2CH_2O]_nCH=CH_2$ |
| 29 | n-Propyl vinyl ether | 764-47-6 | 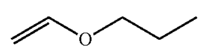 |
| 30 | Tetraethyleneglycol divinyl ether | 83416-06-2 | 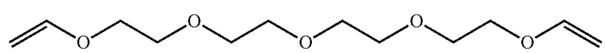 [SMILES: C=COCCOCCOCCOCCOC=C] |
| 31 | Triethyleneglycol methyl vinyl ether | 26256-87-1 | 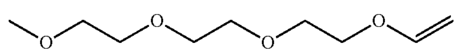 |
| 32 | Trimethylolpropane trivinyl ether | 57758-90-4 | 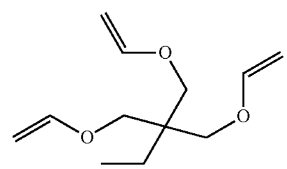 |

Preparation of Labile Maleic Acids

The following reaction scheme represents an example of a reaction used to prepare a LDA

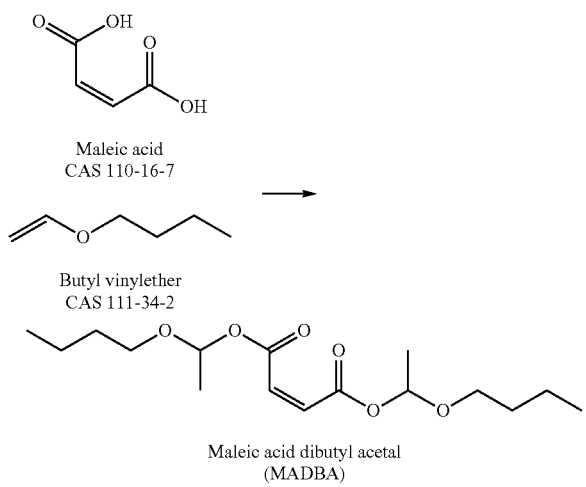

The anaerobic curable composition is based on the (meth) acrylate component, together with an anaerobic cure system, and of course the LDA.

Suitable (meth)acrylate monomers may be chosen from a wide variety of materials, such as those represented by $H_2C=CGCO_2R^1$, where G may be hydrogen, halogen, or alkyl groups having from 1 to about 4 carbon atoms, and $R^1$ may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone, and the like.

Other (meth)acrylate monomers may also be used, such as reaction products of the diglycidylether of bisphenol-A with methacrylic acid and a (meth)acrylate ester corresponding to structure as shown below:

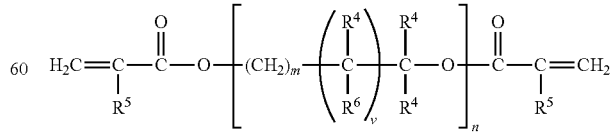

where $R^4$ may be selected from hydrogen, alkyl groups having from 1 to about 4 carbon atoms, hydroxyalkyl groups having from 1 to about 4 carbon atoms or

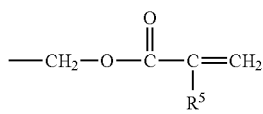

R⁵ may be selected from hydrogen, halogen, and alkyl groups of from 1 to about 4 carbon atoms;

R⁶ may be selected from hydrogen, hydroxy and

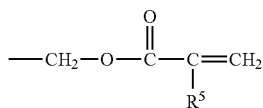

m is an integer equal to at least 1, e.g., from 1 to about 8 or higher, for instance, from 1 to about 4;

v is 0 or 1; and n is an integer equal to at least 1, e.g., 1 to about 20 or more.

Still other (meth)acrylate monomers include silicone (meth)acrylates ("SiMA"), such as those taught by and claimed in U.S. Pat. No. 5,605,999 (Chu), the disclosure of which is hereby expressly incorporated herein by reference.

Additional (meth)acrylate monomers include polyfunctional (meth)acrylate monomers, such as, but not limited to, di- or tri-functional (meth)acrylates like polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylate ("TMPTMA"), diethylene glycol dimethacrylate, triethylene glycol dimethacrylate ("TRIEGMA"), tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate and bisphenol-A mono and di(meth)acrylates, such as ethoxylated bisphenol-A (meth)acrylate ("EBIPMA"), and bisphenol-F mono and di(meth)acrylates, such as ethoxylated bisphenol-F (meth)acrylate.

Combinations of (meth)acrylate monomers may also be used.

The (meth)acrylate component may be present in an amount from about 10 to about 90 percent by weight, such as from about 60 to about 90 percent by weight, based on the total weight of the composition.

Additional components have been included in traditional anaerobic curable compositions to alter the physical properties of either the curable compositions or reaction products thereof, and such additional components may be used in the so-described anaerobic curable compositions.

For instance, one or more of thermal resistance-conferring coreactants (such as maleimides), diluent components reactive at elevated temperature conditions, mono- or poly-hydroxyalkanes, polymeric plasticizers, and chelators (see International Patent Application No. PCT/US98/13704, the disclosure of which is hereby expressly incorporated herein by reference) may be included to modify the physical properties and/or cure profile of the formulation and/or the strength or temperature resistance of the cured adhesive.

When used, the coreactant, reactive diluent, plasticizer, and/or mono- or poly-hydroxyalkanes, may be present in an amount within the range of about 1 percent to about 30 percent by weight, based on the total weight of the composition.

The anaerobic cure system includes a free-radical initiator, such as a peroxide, and optionally, one or more components selected from free-radical accelerators, free-radical inhibitors, as well as metal catalysts, such as iron and copper.

A number of well-known initiators of free radical polymerization are typically incorporated into anaerobic curable compositions including hydroperoxides, such as cymene hydroperoxides ("CHP"), para-menthane hydroperoxide, t-butyl hydroperoxide ("TBH") and t-butyl perbenzoate. Other initiators of free radical polymerization include peroxides, such as benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10% by weight, based on the total weight of the composition, with about 1 to 5% being desirable.

Accelerators of free radical polymerization may also be used in the compositions of the present invention including, without limitation, organic amides and imides, such as benzoic sulfimide (also known as saccharin) (see U.S. Pat. No. 4,324,349). Such accelerators may also be of the hydrazine variety (e.g., acetyl phenyl hydrazine, APH), as disclosed in U.S. Pat. No. 4,287,350 (Rich) and U.S. Pat. No. 4,321,349 (Rich). Conventionally, MA is often added to APH-containing anaerobic cure systems. Here, instead of MA, a LDA is useful instead. Additional specific accelerators include, without limitation, N,N-diethyl-p-toluidine ("DE-p-T") and N,N-dimethyl-o-toluidine ("DM-o-T"). Additional classes of accelerators include thiocaprolactams (e.g., U.S. Pat. No. 5,411,988) and throureas (e.g., U.S. Pat. No. 3,970,505).

When used, accelerators such as saccharin may be present in amounts of about 0.5% to 5% by weight of the total composition.

Stabilizers and inhibitors (such as phenols including hydroquinone and quinones) may also be employed to control and prevent premature peroxide decomposition and polymerization of the composition of the present invention.

Chelating agents, such as the tetrasodium salt of ethylenediamine tetraacetic acid ("EDTA"), may be used to trap trace amounts of metal contaminants. When used, chelating agents may ordinarily be present in the compositions in an amount from about 0.001% by weight to about 0.1% by weight, based on the total weight of the composition.

Metal catalyst solutions or pre-mixes thereof may be used in amounts of about 0.03 to about 0.1% by weight based on the total weight of the composition.

Thickeners, plasticizers, fillers, toughening agents (such as elastomers and rubbers) and other well-known additives may be incorporated herein where the skilled artisan believes it would be desirable to do so.

Also provided are methods of preparing and using the anaerobic curable compositions, as well as reaction products of the compositions.

The anaerobic curable compositions may be prepared using conventional methods that are well known to those persons of skill in the art. For instance, the components may be mixed together in any convenient order consistent with the roles and functions the components are to perform in the compositions. Conventional mixing techniques using known apparatus may be employed.

The anaerobic curable compositions may be applied to a variety of substrates to perform with the desired benefits and advantages described herein. For instance, appropriate substrates may be constructed from steel, brass, copper, aluminum, zinc, and other metals and alloys, ceramics, and thermosets. The compositions of this invention demonstrate particularly good bond strength on surfaces commonly referred to as "active" surfaces, such as iron, brass and copper. An appropriate primer for anaerobic curable compositions may be applied to a surface of the chosen substrate to enhance cure rate.

In addition, a method of preparing an anaerobic curable composition is provided, a step of which includes mixing together a (meth)acrylate component, an anaerobic cure system, and an LDA.

Also provided is a process for bonding using the anaerobic curable composition, the steps of which include applying the composition to a desired substrate surface and exposing the composition to an anaerobic environment for a time sufficient to cure the composition.

In view of the above description, it is clear that a wide range of practical opportunities are provided. The following examples are for illustrative purposes only, and are not to be construed so as to limit in any way the teaching herein.

EXAMPLES

Example 1

Synthesis of Maleic Acid Dibutyl Acetal ("MADBA")

Among the more desirable vinyl ether compounds is butyl vinyl ether. An LDA, maleic acid dibutyl acetal ("MADBA"), was prepared by reacting maleic acid with butyl vinyl ether, as described below.

The selection of butyl vinyl ether as the blocking unit provides the following reaction scheme with MA to form MADBA:

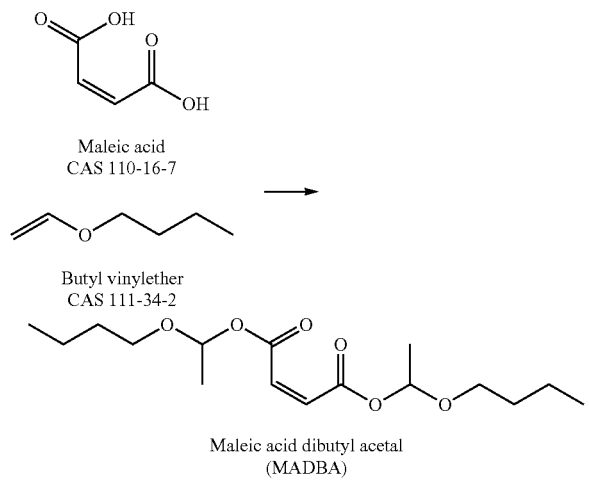

Maleic acid (29.1 g, 400 mmol) and heptane (100 mL) were added to a 500 mL 3-neck round bottom flask ("RBF") equipped with magnetic stirring, nitrogen purge, thermo-controlling, pressure-equilibrated addition funnel, and condenser. Butyl vinyl ether (81.76 g, 800 mmol) was added over a few minutes at ambient temperature. Heptane (100 mL) was then added to the RBF. The mixture was warmed to a temperature of 60° C. Over the next few hours a very mild exotherm was noted.

The reaction was monitored by FT-IR until complete, at which point the reaction was twice washed with water (100 mL), separated, dried over anhydrous magnesium sulfate, gravity filtered, and concentrated in vacuo at a temperature of 40° C. and under a reduced pressure of <50 Torr. The oily product that was recovered was then further dried at that temperature and under a reduced pressure of <1 Torr in a vacuum oven. A clear, colorless oil was obtained in an amount of 123 g, which translates into a 97% yield.

Example 2

The following anaerobic curable compositions were prepared from components and amounts listed in Table II. Composition A represents a control composition that uses maleic acid as an accelerator. Compositions B and C are inventive compositions and has a substantially identical composition to Composition A except the LDA of the present invention is used in place of the free MA, though in each case at different weight percents. Finally, Composition D has substantially the identical composition as Composition A (and Compositions B and C for that matter), except neither free MA nor LDA is present.

TABLE II

| | Composition/(wt %) | | | |
|---|---|---|---|---|
| Component | A | B | C | D |
| PEGMA | 64.23 | 63.71 | 60.43 | 57.66 |
| Tetraethylene glycol di(2-ethylhexoate) | 18.40 | 18.40 | 18.40 | 18.40 |
| Maleic Acid | 0.30 | — | — | — |
| LDA[1] | — | 0.82 | 4.10 | — |
| Napthaquinone[2] | 0.20 | 0.20 | 0.20 | 0.20 |
| EDTA[3] | 1.25 | 1.25 | 1.25 | 1.25 |
| Saccharin | 1.00 | 1.00 | 1.00 | 1.00 |
| APH[4] | 0.15 | 0.15 | 0.15 | 0.15 |
| CHP[5] | 1.00 | 1.00 | 1.00 | 1.00 |
| Resin[6] | 8.47 | 8.47 | 8.47 | 8.47 |
| Polyethylene Powder | 3.00 | 3.00 | 3.00 | 3.00 |
| AEROSIL R972 | 2.00 | 2.00 | 2.00 | 2.00 |
| Total | 100 | 100 | 100 | 100 |

[1]MADBA, added on a percent weight basis that is equimolar in Composition B to the amount of maleic acid used in Composition A and in an amount that is five times that in Composition C;
[2]5% NQ in polyethyleneglycol (meth)acrylate;
[3]3.5% solution;
[4]1-acetyl-2-phenylhydrazine;
[5]cumene hydroperoxide;
[6]Based on TDI, Hydrogentated Bisphenol A, TEGDMA, and HPMA.

As noted from Table II, Compositions A and D are comparative examples, with Composition A using conventional maleic acid as a co-accelerator with APH, and Composition D not using any maleic acid co-accelerator. Compositions B and C include as a labile maleic acid compound, MADBA.

Each of these anaerobic curable compositions was used to bond degreased steel nuts and bolts. Anaerobic cure took place at room temperature. The results of breakaway torque tests (5 replications) in terms of break loose ("BL") and 180 prevail are captured in Table III and shown graphically in FIG. 1.

TABLE III

| Composition | Time (hours) | | | | | | | |
|---|---|---|---|---|---|---|---|---|
| | 0.5 | | 1 | | 4 | | 24 | |
| | BL | 180 Prevail | BL | 180 Prevail | BL | 180 Prevail | BL | 180 Prevail |
| A | 83 | 36 | 97 | 53 | 122 | 54 | 146 | 79 |
| B | 63 | 45 | 111 | 47 | 111 | 66 | 168 | 70 |
| C | 32 | 5 | 87 | 27 | 136 | 40 | 168 | 45 |
| D | 45 | 34 | 43 | 47 | 57 | 46 | 84 | 71 |

As can be seen from Table III, Composition A shows anaerobic cure when MA is present, as would be expected. Composition B shows that anaerobic cure releases the cure accelerator (MA) initially, as it cure time approaches 24 hours. Composition C shows anaerobic cure with four times the amount used in Composition C of MADBA appears to be stunted initially but is later offset over time as anaerobic cure continues over the 24 hour cure period. Both Compositions B and C show the beneficial torque strength improvement. Composition D shows the lack of strength development with MA or an LDA not present.

What is claimed is:

1. An anaerobic curable composition comprising;
   (a) a (meth)acrylate component;
   (b) an anaerobic cure system; and
   (c) the reaction product of a vinyl ether compound and maleic acid.

2. The composition of claim 1 wherein the (meth)acrylate component is represented by: $H_2C=CGCO_2R^1$, wherein G may be hydrogen, halogen, or alkyl groups having from 1 to about 4 carbon atoms, and R1 may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate and sulfone;

reaction products of the diglycidylether of bisphenol-A with methacrylic acid and a (meth)acrylate ester corresponding to structure as shown below:

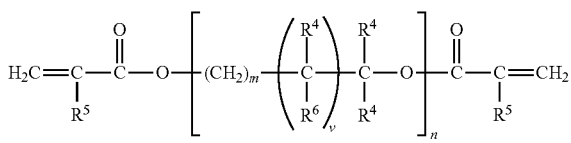

wherein $R^4$ may be selected from hydrogen, alkyl groups having from 1 to about 4 carbon atoms, hydroxyalkyl groups having from 1 to about 4 carbon atoms or

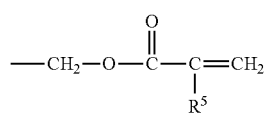

$R^5$ may be selected from hydrogen, halogen, and alkyl groups of from 1 to about 4 carbon atoms;

$R^6$ may be selected from hydrogen, hydroxy and

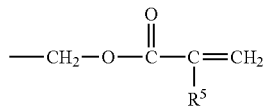

m is an integer equal to at least 1;
v is 0 or 1; and
n is an integer equal to at least 1; and polyfunctional (meth)acrylate monomers, di- or tri-functional (meth)acrylates, polyethylene glycol di(meth) acrylates, tetrahydrofuran (meth)acrylates and di(meth) acrylates, hydroxypropyl (meth)acrylate, hexanediol di(meth)acrylate, trimethylol propane tri(meth)acrylate, diethylene glycol dimethacrylate, triethylene glycol dimethacrylate, tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate, bisphenol-A mono and di(meth)acrylates, ethoxylated bisphenol-A (meth)acrylate, and bisphenol-F mono and di(meth)acrylates, and ethoxylated bisphenol-F (meth)acrylate.

3. The composition of claim 1 wherein the anaerobic cure system comprises a free-radical initiation and optimally one or more free-radical accelerators.

4. A composition comprising the reaction product of:
   (a) a (meth)acrylate component;
   (b) an anaerobic cure system; and
   (c) the reaction product of a vinyl ether compound and maleic acid.

5. The composition of claim 1 wherein the vinyl ether compound is selected from one or more of ethyl vinyl ether; isobutyl vinyl ether; n-butyl vinyl ether; tert-butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tert-amyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether.

6. A method of making an anaerobic curable composition comprising;
   (i) Providing a composition comprising:
      (a) a (meth)acrylate component; and
      (b) an anaerobic cure system; and
   (ii) Adding to the composition of step (i) the reaction product of a vinyl ether compound and maleic acid.

* * * * *